(12) United States Patent  
Sugimoto

(10) Patent No.: US 7,811,229 B2  
(45) Date of Patent: Oct. 12, 2010

(54) ELECTRONIC ENDOSCOPE SYSTEM FOR FLUORESCENCE OBSERVATION

(75) Inventor: Hideo Sugimoto, Tokyo (JP)

(73) Assignee: Hoya Corporation, Tokyo (JP)

( * ) Notice: Subject to any disclaimer, the term of this patent is extended or adjusted under 35 U.S.C. 154(b) by 1176 days.

(21) Appl. No.: 11/168,304

(22) Filed: Jun. 29, 2005

(65) Prior Publication Data

US 2005/0288556 A1    Dec. 29, 2005

(30) Foreign Application Priority Data

Jun. 29, 2004    (JP) ............................. 2004-191931

(51) Int. Cl.
*A61B 1/06*    (2006.01)

(52) U.S. Cl. ...................... 600/160; 600/476

(58) Field of Classification Search ................ 600/118, 600/472, 473, 475, 477, 160, 178, 181, 476

See application file for complete search history.

(56) References Cited

U.S. PATENT DOCUMENTS

| | | | |
|---|---|---|---|
| 5,642,157 A | | 6/1997 | Shibanuma |
| 5,749,830 A | * | 5/1998 | Kaneko et al. ............... 600/160 |
| 6,099,466 A | | 8/2000 | Sano et al. |
| 6,602,186 B1 | * | 8/2003 | Sugimoto et al. ............ 600/126 |
| 6,635,011 B1 | * | 10/2003 | Ozawa et al. ................ 600/178 |
| 6,663,561 B2 | * | 12/2003 | Sugimoto et al. ............ 600/160 |
| 2002/0013512 A1 | * | 1/2002 | Sendai et al. ................ 600/160 |
| 2002/0026099 A1 | * | 2/2002 | Adachi et al. ................ 600/178 |
| 2002/0062061 A1 | * | 5/2002 | Kaneko et al. ............... 600/118 |
| 2002/0147384 A1 | * | 10/2002 | Uchikubo .................... 600/109 |
| 2002/0161282 A1 | * | 10/2002 | Fulghum ..................... 600/160 |
| 2004/0085441 A1 | * | 5/2004 | Onishi et al. .................. 348/65 |

FOREIGN PATENT DOCUMENTS

JP    2-131740    5/1990

(Continued)

OTHER PUBLICATIONS

English language Abstract of JP 9-66023.

(Continued)

*Primary Examiner*—Linda C Dvorak
*Assistant Examiner*—Samuel Candler
(74) *Attorney, Agent, or Firm*—Greenblum & Bernstein, P.L.C.

(57) ABSTRACT

An electronic endoscope system, which is adapted to observe a fluorescence image of autofluorescence emitted from a body cavity wall irradiated with excitation light, includes a controller that controls a light source apparatus to alternately introduce either white light or excitation light into a light guide while taking a normal color image and the fluorescence image, and controls an image signal generating system to generate normal color image signals and fluorescence image signals. The controller further controls a display device to display a still fluorescence image in a first window defined on a displaying area thereof based on the fluorescence image signals which have been generated when a still image switch is turned ON during the time to take the fluorescence image, and simultaneously to display a moving normal color image in a second window defined on a displaying area thereof based on the normal color image signals generated every time the body cavity wall is intermittently illuminated with the white light, the first window being larger than the second window.

15 Claims, 6 Drawing Sheets

FOREIGN PATENT DOCUMENTS

| | | |
|---|---|---|
| JP | 7-194532 | 8/1995 |
| JP | 9-66023 | 3/1997 |
| JP | 2001-137183 | 5/2001 |
| JP | 2002-291692 | 10/2002 |
| JP | 2002-291694 | 10/2002 |
| JP | 2003-33324 | 2/2003 |

OTHER PUBLICATIONS

English language Abstract of JP 7-194532.
U.S. Appl. No. 11/186,905 to Sugimoto, filed Jul. 22, 2005.
U.S. Appl. No. 11/168,463 to Sugimoto, filed Jun. 29, 2005.
English language Abstract of JP 2002-291694.

* cited by examiner

ELECTRONIC ENDOSCOPE SYSTEM FOR FLUORESCENCE OBSERVATION

BACKGROUND OF THE INVENTION

The present invention relates to an electronic endoscope system that is adapted to observe a fluorescence image of autofluorescence emitted from a body cavity wall irradiated with excitation light, as well as a normal image of the body cavity wall illuminated with white light, on a display device such as a monitor.

An example of such an electronic endoscope system is disclosed in Japanese Patent Provisional Publications No. HEI 9-066023. The system disclosed in this publication includes a first solid-state imaging device for capturing a fluorescence image, and a second solid-state imaging device for capturing an RGB color image in accordance with a frame sequential method. In the system, signals outputted from the first and second solid-state imaging devices are processed by a video circuit for fluorescence images and a video circuit for normal images. The signals are then synthesized by an image synthetic circuit, and are displayed on a monitoring device. According to the operation of a display image selector switch, one or both of the two kinds of images are displayed on the monitoring device.

In the above-described conventional system, as blue light is used for illuminating an object when either the fluorescence image or the normal image is captured, two solid-state imaging devices must be used in order to capture both kinds of images (i.e., the fluorescence image and the normal image) simultaneously.

Moreover, although it is sometimes necessary that a fluorescence image is displayed as a still image, there is no disclosure in the above publication that the fluorescence image is displayed as a still image.

Another example is disclosed in Japanese Patent Provisional Publication No. P2003-33324A. FIG. 10 shows a block diagram of the system that is illustrated in FIG. 16 of this publication. The system disclosed in this publication includes (see FIG. 10) a first lamp 124 that emits illuminating light for normal observation and a second lamp 125 that emits excitation light, and either one of the two kinds of light is selectively introduced into a light guide 133 by changing the position of a movable mirror 128. Image signals captured by a CCD 137 are stored in a first memory 141 and a second memory 142, and are then displayed on a Hi-Vision monitor 115 through a display location selector circuit 144. When a selector switch for displaying two images (hereinafter, referred to as a two-image-display switch) is turned ON, a normal image and a fluorescence image are displayed on the Hi-Vision monitor 115, simultaneously. That is, when the two-image-display switch is turned ON, the mirror 128 turns to the position indicated by a solid line, and the excitation light is introduced into the light guide 133. At the same time, the normal image, which has been inputted into the first memory immediately before the first memory becomes write-protected, is outputted therefrom repeatedly and displayed as a still image. On the other hand, a shutter 132 closes after excitation light irradiation for a predetermined period of time, and the signal of the fluorescence image taken at this time is stored in the second memory. The second memory then becomes write-protected, and the signals of the fluorescence image are outputted therefrom repeatedly and displayed as a still image. Then, when the mirror 28 returns to the position indicated by a dotted line and the shutter opens, the normal image taken with the illuminating light emitted from the first lamp 124 is stored sequentially in the first memory 141 and displayed as a moving image.

This system allows either the normal illuminating light or the excitation light to be selectively applied by moving the mirror 128, and thereby, the fluorescence image and the normal image can be captured by a single imaging device (CCD 137). However, it takes such a long fixed period of time (t seconds) for the mirror 128 to turn and return that both kinds of images cannot be displayed simultaneously as moving images.

Additionally, it is disclosed in this publication that the fluorescence image and the normal image are displayed as a still image and a moving image, respectively, when the two-image-display switch is turned ON. However, as described and in view of the configuration as disclosed, the normal image must be displayed not as a moving image but as a still image during the time period after the two-image-display switch has been turned ON. Therefore, it is impossible to move an endoscope tip and observe other parts during the time period.

Further, the fluorescence image is typically used to identify a pathological part, while the normal image is referred to for moving the endoscope tip. Therefore, it is preferable that the fluorescence image is displayed as large as possible, while the normal image, during such a fluorescence observation, need not be displayed as a larger image. In each of the above two publications, however, the fluorescence image and the normal image are displayed in the same size.

SUMMARY OF THE INVENTION

The present invention is advantageous in that an electronic endoscope system is provided that is capable of displaying a normal image as a moving image immediately after displaying a still fluorescence image when an operator observing a moving fluorescence image operates the endoscope system to display the still fluorescence image.

According to an aspect of the invention, there is provided an electronic endoscope system used for observing living tissues inside a body cavity, which is provided with a single imaging device that receives an optical image and outputs an image signal corresponding to the received optical image, an illuminating device having a white light source emitting white light and an excitation light source that emits excitation light having a predetermined wavelength, the living tissues emitting autofluorescence when irradiated with the excitation light, an image forming system that forms the optical image of the living tissues illuminated with each of the white light and the excitation light on the imaging device, an illuminating control system that controls the illuminating device such that the white light source and the excitation light source illuminate the living tissues alternately at every predetermined period, an image processing system that receives the image signal outputted by the single imaging device, the image processing system obtaining a normal image when the living tissues are illuminated with the white light and a fluorescence image when the living tissues are irradiated with the excitation light, a display device configured to display the normal image and the fluorescence image, and a display control system that controls the display device such that the normal image is displayed in a first displaying area of the display device and the fluorescence image is displayed in a second displaying area, the predetermined period being determined so that the color image and the fluorescence image appear to be displayed simultaneously as moving images.

Optionally, the controller may control the display device to display the still fluorescence image in a first window defined on a displaying area thereof and the moving normal image in a second window defined on the displaying area thereof when the still image switch is operated during the time to take the fluorescence image, the first window being larger than the second window.

Further optionally, the second window may be included in the first window.

Still optionally, the light source apparatus may include a rotary shutter inserted between the white light source and the light guide, the rotary shutter having a light transmitting area and a light blocking area, the white light being intermittently incident on the light guide as the rotary shutter rotates.

Furthermore, the light source apparatus may include an excitation light source driver that intermittently turns ON/OFF the excitation light source synchronously with the blocking/transmitting operation of the rotary shutter.

Preferably, the rotary shutter may be able to be shifted together with a beam combiner to a point that the rotary shutter does not interfere with the white light, the beam combiner combining both light paths of the white light and the excitation light.

Optionally, the image signal generating system may include a pre-signal-processing circuit that processes the image signals received from the imaging device, at least two image memories that temporarily store the image signals outputted from the pre-signal-processing circuit, and a post-signal-processing circuit that transforms the image signals outputted from the image memories into standardized video signals which are allowed to be displayed on the display device.

Further optionally, the controller may include a system controller that controls the whole system, and a timing controller that takes timing control of the imaging device, the light source apparatus, the image signal generating system, and the display device based on commands from the system controller, the timing controller controlling the intended ones of the image memories to be write-protected at the time the still image switch is operated while taking the fluorescence image and to output repeatedly fluorescence image signals which have been inputted thereinto immediately before the time, and, at the same time, may further control the display device to display the still fluorescence image based on the fluorescence image signals.

Still optionally, the endoscope may include an objective lens that is provided to the insertion part, and an excitation light cut filter that is provided between the objective lens and the imaging device, the excitation light cut filter eliminating the wavelength components equivalent to the excitation light from light directed to the imaging device from the objective lens.

In this case, the excitation light source may emit near-ultraviolet light.

According to another aspect of the invention, there is provided an electronic endoscope system used for observing living tissues inside a body cavity, which includes a single imaging device that receives an optical image and outputs an image signal corresponding to the received optical image, an illuminating device having a white light source emitting white light, an excitation light source that emits excitation light having a predetermined wavelength, the living tissues emitting autofluorescence when irradiated with the excitation light, an image forming system that forms an optical image of the living tissues illuminated with each of the white light and the excitation light on the imaging device, an image processing system that receives the image signal outputted by the single imaging device, the image processing system obtaining a normal image when the living tissues are illuminated with the white light and a fluorescence image when the living tissues are irradiated with the excitation light, a display device configured to display the normal image and the fluorescence image on a first display area and a second display area on the display device, respectively, and an operable member to be operated by a user when a still image is to be displayed on the display device. When a moving fluorescence image is displayed on the display device, the white light source may be powered OFF and the excitation light source is powered ON. Further, if the operable member is operated when the moving fluorescence image is displayed on the display device, the excitation light source may be powered OFF and the white light source is turned ON, the fluorescence image which was obtained immediately before the excitation light source is powered OFF being repeatedly displayed on the second display area of the display device as a still fluorescence image, the imaging device outputting the image signal corresponding to the optical image of the living tissues illuminated with the white light, the image processing system obtaining the normal image of the living tissues which is displayed on the first display area of the display device, the normal image and the fluorescence image appearing to be displayed on the display device simultaneously.

Optionally, the second display area may include the first display area.

Further optionally, the image signal generating system may include a pre-signal-processing circuit that processes the image signals received from the imaging device, at least two image memories that temporarily store the image signals outputted from the pre-signal-processing circuit, and a post-signal-processing circuit that transforms the image signals outputted from the image memories into standardized video signals which are allowed to be displayed on the display device.

Still optionally, the controller may include a system controller that controls the whole system, and a timing controller that takes timing control of the imaging device, the light source apparatus, the image signal generating system, and the display device based on commands from the system controller, the timing controller controlling the intended ones of the image memories to be write-protected at the time the still image switch is operated while taking the fluorescence image and to output repeatedly fluorescence image signals which have been inputted thereinto immediately before the time, and, at the same time, may further control the display device to display the still fluorescence image in the first window based on the fluorescence image signals.

Furthermore, the endoscope may include an objective lens that is provided to the insertion part, and an excitation light cut filter that is provided between the objective lens and the imaging device, the excitation light cut filter eliminating the wavelength components equivalent to the excitation light from light directed to the imaging device from the objective lens.

Optionally, the excitation light source may emit near-ultraviolet light.

According to another aspect of the invention, there is provided an electronic endoscope system that is provided with an electronic endoscope including an insertion part to be inserted in a body cavity, a light guide which transmits light to the tip of the insertion part through the insertion part, and an imaging device which receives light from a body cavity wall illuminated with light transmitted by the light guide, a light source apparatus including a white light source and an excitation light source, the body cavity wall emitting autofluorescence when illuminated with the excitation light, the light source being configured such that the white light and the excitation light are selectively introduced into the light guide, an image signal generating system having an imaging device that receives an optical image and outputs an image signal corresponding to the received optical image, the image signal generating system generating a normal image signal from the image signal outputted from the imaging device when the body cavity wall is illuminated with the white light, the image signal generating system generating a fluorescence image signal from the image signals outputted from the imaging device when the body cavity wall is illuminated with the excitation light, a display device that is configured to display images in accordance with image signals outputted from the image signal generating system, and a controller that controls the light source apparatus to alternately introduce the white light and the excitation light into the light guide when the electronic endoscope operates in a first mode, the image signal generating system generating both the normal image signals and the fluorescence image signals when the electronic endoscope operates in the first mode, the controller controlling the light source apparatus to introduce only the white light into the light guide when the electronic endoscope operates in a second mode, the display device displaying a still fluorescence image based on the fluorescence image signal which has been generated immediately before the operation mode was switched to the second mode, the display device displaying a moving normal image based on the normal image signal when the body cavity wall is illuminated with the white light.

According to a further aspect of the invention, there is provided an electronic endoscope system used for observing living tissues inside a body cavity, which includes an electronic endoscope including an insertion part to be inserted in the body cavity, a light guide which transmits light to the tip of the insertion part through the insertion part, and an imaging device which receives light from the living tissues illuminated with light transmitted by the light guide, an illuminating device having a white light source emitting white light and an excitation light source that emits excitation light having a predetermined wavelength, the living tissues emitting autofluorescence when irradiated with the excitation light, an image forming system that forms an optical image of the living tissues illuminated with the white light and the excitation light on the imaging device, an image processing system that obtains a normal image when the living tissues are illuminated with the white light and a fluorescence image when the living tissues are irradiated with the excitation light, a display device configured to display the normal image and the fluorescence image, and a controller that controls the illuminating device to alternately introduce the white light and the excitation light into the light guide when the electronic endoscope operates in a first mode, the image processing system generating both the normal image signals and the fluorescence image signals when the electronic endoscope operates in the first mode, the controller controlling the illuminating device to introduce only the white light into the light guide when the electronic endoscope operates in a second mode. The display device may be configured to display a still fluorescence image based on the fluorescence image signal which was generated immediately before the operation mode was switched to the second mode, the display device displaying a moving normal image based on the normal image signal when the body cavity wall is illuminated with the white light.

BRIEF DESCRIPTION OF THE ACCOMPANYING DRAWINGS

DETAILED DESCRIPTION OF THE EMBODIMENTS

Hereinafter, an electronic endoscope system according to an embodiment of the present invention will be described with reference to the accompanying drawings. The electronic endoscope system of the embodiment is directed to a system that is adapted to observe a fluorescence image of autofluorescence emitted from a body cavity wall irradiated with excitation light on a display device such as a monitor, as well as a normal image of the body cavity wall illuminated with white light.

Figure 1:
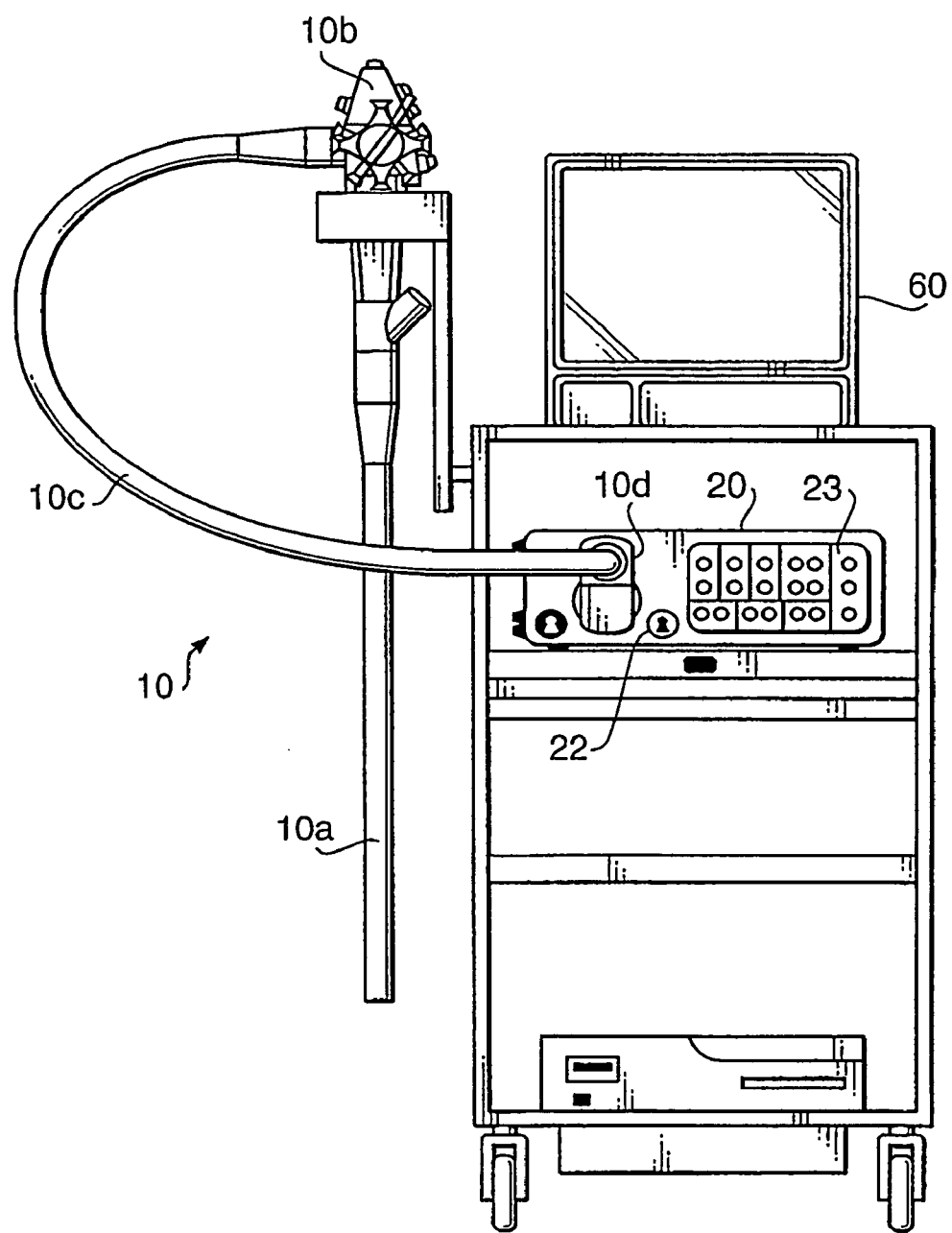
FIG. 1 is a front view of an electronic endoscope system according to an embodiment of the invention.
Figure 2:
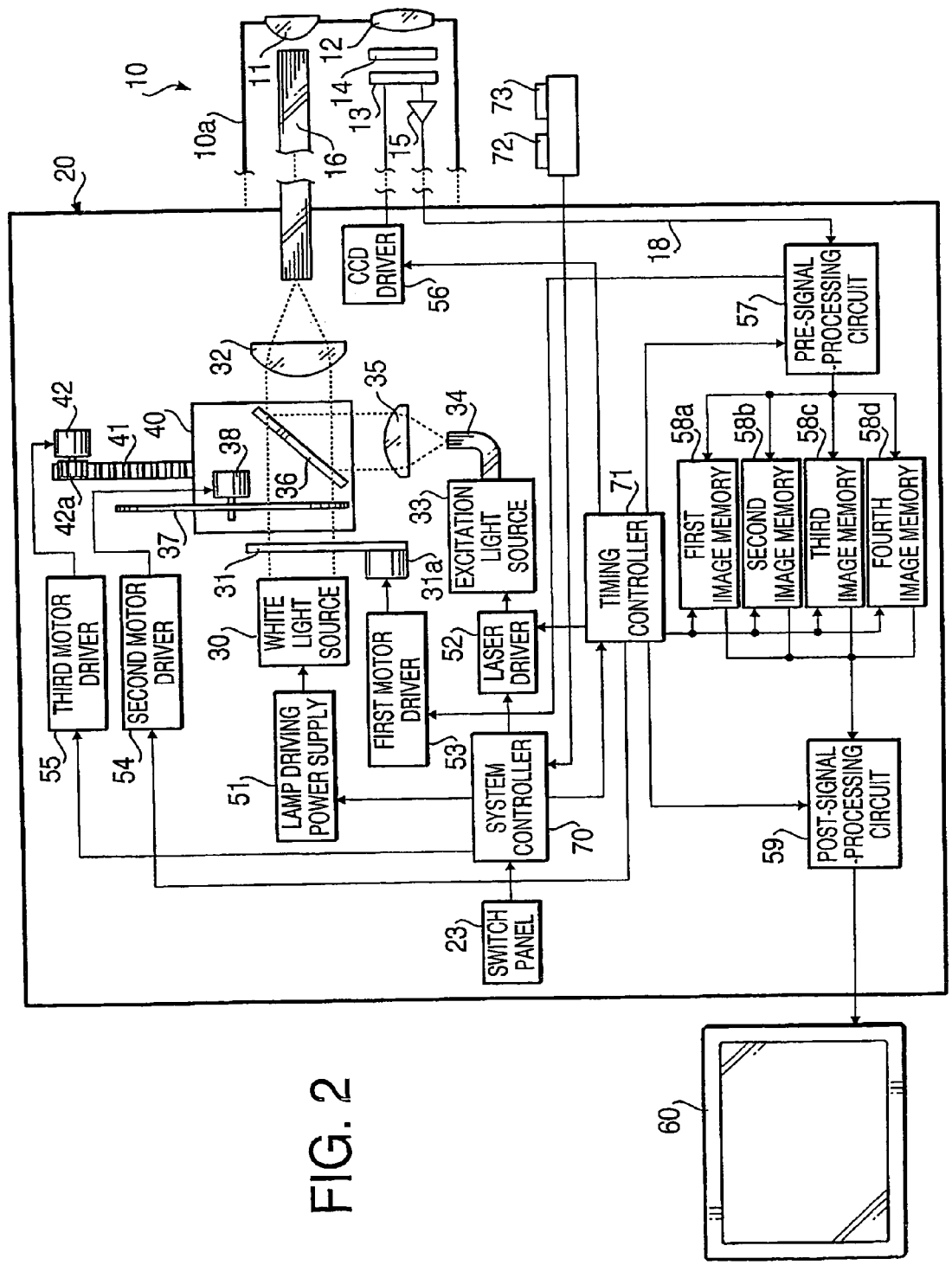
FIG. 2 is a block diagram illustrating an internal constitution of the electronic endoscope system shown in FIG. 1, especially showing a layout in the case of fluorescence observation.

FIG. 1 schematically shows an external view of an electronic endoscope system 1 according to an embodiment of the invention, and FIG. 2 shows a block diagram illustrating an internal constitution of the electronic endoscope system 1. As shown in FIG. 1, the electronic endoscope system 1 is provided with a fluorescence observation endoscope 10, a light source apparatus 20, and a monitor 60.

The fluorescence observation endoscope 10, which is adapted to fluorescence observation by modifying a usual electronic endoscope, is provided with an insertion part 10a that is formed long and slender so as to be inserted into the body cavity and has a flexible bendable part at the tip thereof, an operating part 10b that includes an angle knob and the like to operate the bendable part of the insertion part 10a, a flexible light guide tube 10c that connects the operating part 10b with a light source apparatus 20, and a connector 10d that is provided at the rear anchor of the flexible light guide tube 10c.

The light source apparatus 20 supplies illuminating light and excitation light to the fluorescence observation endoscope 10, and, as described in detail below, has a function as an image signal generator that generates image signals from signals taken by the fluorescence observation endoscope 10 and a function as a controller that controls the monitor 60 to display each of a fluorescence image and a normal image in corresponding one of main and sub windows according to a setting. On the front surface of the light source apparatus 20, there are provided a key switch 22 for ON/OFF operation of a main power supply thereof, and a switch panel 23 on which various kinds of operation switches are arranged.

Hereinafter, according to FIG. 2, the constitutions of the fluorescence observation endoscope 10 and the light source apparatus 20 are explained in sequence. On the distal end surface of the insertion part 10a of the fluorescence observation endoscope 10, there are provided a light distribution lens 11 and an objective lens 12. Inside the tip portion of the insertion part 10a, there are incorporated an imaging device such as a CCD color imaging sensor that takes an object's color image formed by the objective lens 12, an excitation light cut filter 14 that eliminates the wavelength components equivalent to the excitation light for fluorescence excitation from the wavelength components of light directed to the imaging device 13 from the objective lens 12, and a cable driver 15 that amplifies image signals outputted from the imaging device 13.

Figure 3:
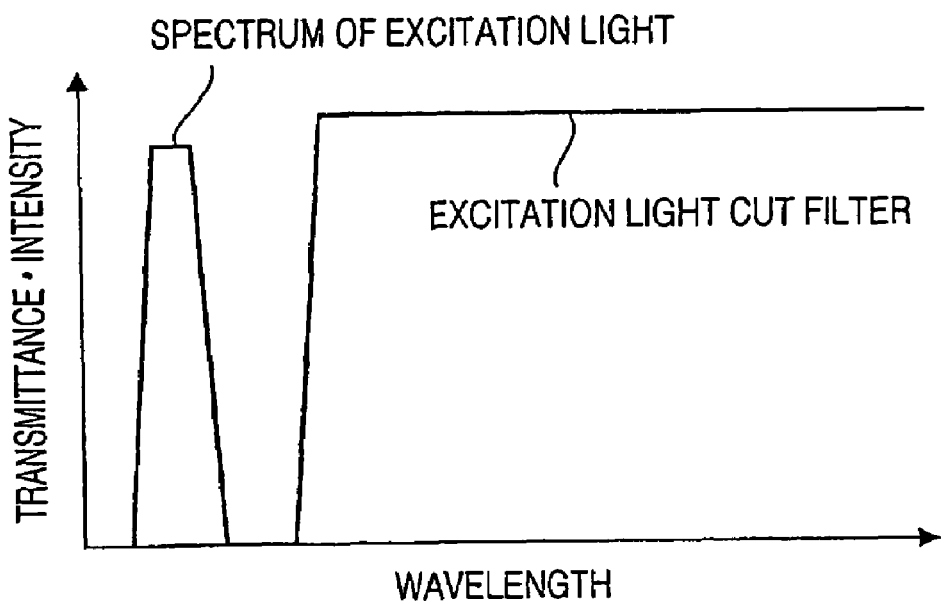
FIG. 3 is a graph illustrating transmission characteristics of an excitation light cut filter provided in an optical system in FIG. 2.

As shown in FIG. 3, the excitation light cut filter 14 has characteristics that cut off the excitation light and transmit light with wavelengths longer than the excitation light. Therefore, it is possible to prevent the excitation light, which is reflected by the wall of the body cavity subject to the observation, from being introduced into the imaging device 13 and to take only the fluorescence images during fluorescence observation. In addition, since near-ultraviolet light that excites autofluorescence of a living organism is applied as excitation light, even if the wavelength components of the excitation light is cut off by the excitation light cut filter 14, there is no trouble in taking a blue component, which is also generally used as excitation light, while taking normal color images.

A signal cable 18 that transmits the image signals amplified by the cable driver 15 runs through the insertion part 10a, the operation part 10b, and the flexible light guide tube 10c, and is connected to a signal processing circuit of the light source apparatus 20 that is connected to the fluorescence observation endoscope 10.

In parallel with the signal cable 18, a light guide 16 that is constituted by bundling a plurality of optical fibers runs through the insertion part 10a, the operation part 10b, and the flexible light guide tube 10c. The tip end face of the light guide 16 faces the light distribution lens 11 within the tip portion of the insertion part 10a, and the rear anchor of the light guide 16 is fixed in the state to be inserted into the light source apparatus 20.

The light source apparatus 20 selectively introduces either white light for observation of the body cavity wall or the excitation light that excites the living tissues of the body cavity wall so that the living tissues emits autofluorescence into the end face of the rear anchor of the light guide 16. The light source apparatus 20 further processes the image signals received from the cable driver 15 to generate video signals, and then outputs the video signals to the monitor 60.

An optical system of the light source apparatus 20 is provided with a white light source (discharge tube lamp) 30 that emits substantially parallel white light (white light), a light control aperture 31 that controls the beam diameter of the white light emitted from the white light source 30, a condenser lens 32 that converges the white light which is transmitted through the light control aperture 31 on the end face of the rear anchor of the light guide 16, an excitation light source 33 that emits the excitation light, an optical waveguide (single fiber) 34 that guides the excitation light emitted from the excitation light source 33, a collimating lens 35 that collimates the excitation light, which is diverging light emitted from the optical waveguide 34, and a dichroic mirror 36 that combines both light paths of the white light and the excitation light.

The light control aperture 31 is driven by an aperture driving motor 31a, and functions to control the intensity of the white light according to the reflectance of an object. The white light path that extends straight from the white light source 30 to the light guide 16 and the excitation light path that intersects perpendicularly therewith are combined by the light path combining device, that is, the dichroic mirror 36. Since the dichroic mirror 36 transmits the white light and reflects the near-ultraviolet light with wavelengths shorter than the white light, the dichroic mirror 36 transmits major part of the white light and reflects the excitation light, introducing both kinds of light into a single light path that extends to the end face of the rear anchor of the light guide 16.

Figure 4:
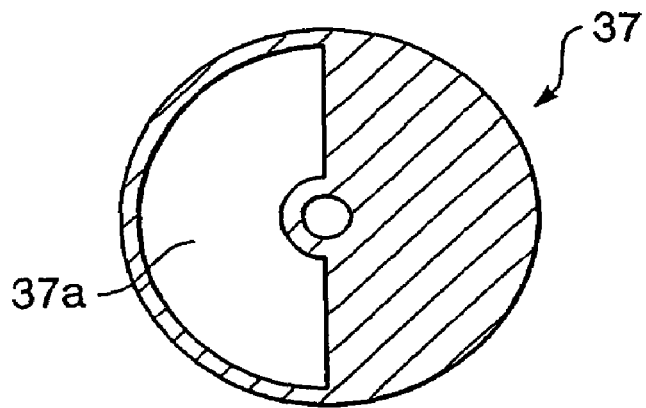
FIG. 4 is a front view of a rotary shutter provided in the optical system in FIG. 2.

Between the white light source 30 and the dichroic mirror 36, there is arranged a rotary shutter 37 that enables the intermittent ON/OFF operation of the white light (that is, intermittently transmits or blocks the white light). The rotary shutter 37, as a front view thereof is shown in FIG. 4, has a fan-shaped window 37a with a center angle of 180 degrees, and the size of the window 37a is configured to be larger than the diameter of the beam of the white light. The rotary shutter 37 is allowed to rotate and intermittently transmit the white light as a shutter driving motor 38 is driven.

In addition, the dichroic mirror 36, the rotary shutter 37, and the shutter driving motor 38 are arranged in a unit 40 that is movable in the up-and-down direction in FIG. 2, that is, in the direction perpendicular to the white light path. A rack gear 41 extending along the moving direction thereof is fixed to the unit 40, and is geared with a pinion 42a of a unit driving motor 42. Rotating the unit driving motor 42 allows the unit 40 to move monolithically in the up-and-down direction so that the dichroic mirror 36 and the rotary shutter 37 can be shifted between both positions on and out of the white light path.

The light source apparatus 20 is provided with a lamp driving power supply 51 that supplies current to the white light source 30, a laser driver 52 that drives and switches the excitation light source 33, a first motor driver 53 that drives the aperture driving motor 31a, a second motor driver 54 that drives the shutter driving motor 38, a third motor driver 55 that drives the unit driving motor 42, and a CCD driver 56 that drives the imaging device 13. The light source apparatus 20 further includes a pre-signal-processing circuit 57 that processes image signals received from the cable driver 15, a first-fourth image memories 58a, 58b, 58c, and 58d that temporarily store digital image signals outputted from the pre-signal-processing circuit 57, a post-signal-processing circuit 59 that transforms the digital image signals outputted from the image memories into standardized video signals which are allowed to be displayed on a television monitor and outputs the standardized video signals, and a system controller 70 and a timing controller 71 that control all of the above components.

The system controller 70 is connected with a still image switch 72 and a fluorescence mode switch 73 that are provided at the operation part 10b, and further is connected electrically with various switches that are arranged on the switch panel 23. Based on the setting of each switches, the system controller 70 controls the lamp driving power supply 51 and the laser driver 52 so that the white light and the excitation light are consecutively emitted or stopped, and further controls the third motor driver 55 that drives the unit driving motor 42 to change the location of the unit 40.

Based on a command from the system controller 70, the timing controller 71 controls the laser driver 52 to carry out the intermittent ON/OFF operation of the excitation light at predetermined timing, and further controls the second motor driver 54 that drives the shutter driving motor 38 to carry out the intermittent ON/OFF operation of the white light at predetermined timing. The timing controller 71 also controls the timing when the imaging device 13 takes an image through the CCD driver 56, and further controls the data read/write operation of each of the image memories 58a-58d (the address data controls), indicating the respective timings of the image signal processing for the pre-signal-processing circuit 57 and the post-signal-processing circuit 59. In addition, the pre-signal-processing circuit 57 controls the first motor driver 53 that drives the aperture driving motor 31 to adjust the intensity of the white light and the brightness of the normal image on the monitor 60 according to the brightness level of the image signals inputted during the time to take a normal image.

Next, the operation of the endoscope system of the embodiment constituted as mentioned above is explained. The endoscope system of the embodiment operates in any one of the following three modes as moving image modes: a normal image display mode in which the normal (color) image taken with the white light applied continuously is displayed as a moving image; a fluorescence image display mode in which the fluorescence image taken with the excitation light applied continuously is displayed as a moving image; and a simultaneous display mode in which the normal image and the fluorescence image taken with the white light and the excitation light alternately applied are displayed as moving images. When a fluorescence mode switch 73 provided at the operation part 10b of the fluorescence observation endoscope 10 is OFF, the system is set up in the normal image display mode. If the fluorescence mode switch is turned ON, the system will be set up in either the fluorescence image display mode or the simultaneous display mode. In this case, the mode to be selected may be previously defined with the switches that are provided on the switch panel 23.

Furthermore, when the still image switch is pushed in the normal image display mode, the still normal image is displayed in the main window, and the moving normal image is displayed in the sub window having a display area smaller than that of the main window. When the still image switch is pushed in the fluorescence image display mode or the simultaneous display mode, the still fluorescence image is displayed in the main window, and the moving normal image in the sub window.

When the fluorescence mode switch 73 is OFF, the system is set up in the normal image display mode, as described above. In the normal image display mode for the normal observation, the system controller 70 controls the third motor driver 55 to drive the unit driving motor 42 and shift the unit 40 to a point out of the white light path, and further controls the lamp driving power supply 51 to let the white light source 30 emit the white light continuously. At this time, the shutter driving motor 38 and the excitation light source 33 are not driven, but still OFF. Thereby, the white light emitted from the white light source 30 is continuously introduced into the light guide 16. The imaging device 13 provided at the tip of the fluorescence observation endoscope captures the image of the inside of the body cavity illuminated with the white light. The normal image signals outputted from the imaging device 13 are inputted into the pre-signal-processing circuit 57 through the cable driver 15 and the signal cable 18.

The pre-signal-processing circuit 57, based on the signals from the timing controller 71, allows the first image memory 58a and the second image memory 58b to store the normal image signals. The post-signal processing circuit 59, based on the signals from the timing controller 71, reads out the image signals from the first image memory 58a and the second image memory 58b, and converts the image signals to the video signals, displaying a single normal image as a moving image on the monitor 60.

Figure 5:
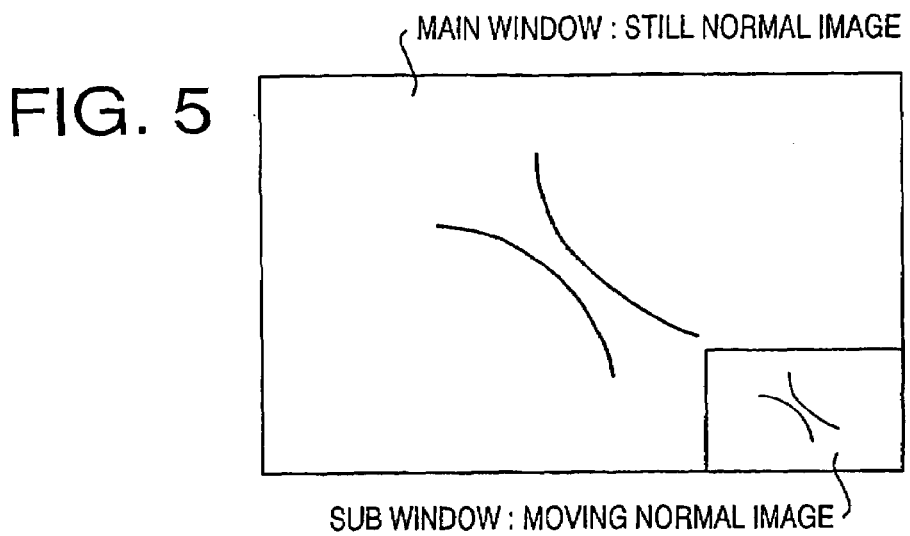
FIG. 5 shows an example of a screen displayed on a monitor when a still image switch is turned ON in a normal image display mode.

When the still image switch 72 is turned ON in the normal image display mode, the system controller 70 keeps the location of the unit 40 out of the white light path, and the timing controller 71 forbids to write the image signals to the first and second memories 58a, 58b, and allows the imaging device 13 to keep taking the image, and further allows the third and fourth memories 58c, 58d to store the image signals. The post-signal-processing circuit 59, based on the signals from the timing controller 71, reads out the same signals from the first and second memories 58a, 58b repeatedly to display the still normal image in the main window, and further reads out the signals rewritten sequentially from the third and fourth memories 58c, 58d to generate the video signals of the moving normal image, which are displayed in the sub window on the monitor 60. FIG. 5 shows an example of a screen that is displayed on the monitor 60 when the still image switch is turned ON in the normal image display mode.

If the fluorescence mode switch 73 is turned ON in the normal image display mode, the system will be set up in either mode between the fluorescence image display mode and the simultaneous display mode, the mode which is previously defined by the switches on the switch panel 23. When the system is set up in the fluorescence image display mode by the switches on the switch panel 23, the system controller 70 controls the third motor driver 55 to drive the unit driving motor 42 so that the unit 40 is shifted to a point on the white light path, and controls the lamp driving power supply 51 to turn OFF the white light source 30, and further controls the laser driver 52 to let the excitation light source 33 emit the excitation light continuously. The shutter driving motor 38 is still OFF. Thereby, the excitation light emitted from the excitation light source 33 is continuously introduced into the light guide 16. The imaging device 13 provided at the tip of fluorescence observation endoscope captures the image of fluorescence emitted from the body cavity excited by the excitation light. The fluorescence image signals outputted from the imaging device 13 is inputted into the pre-signal-processing circuit 57 through the cable driver 15 and the signal cable 18.

Figure 6:
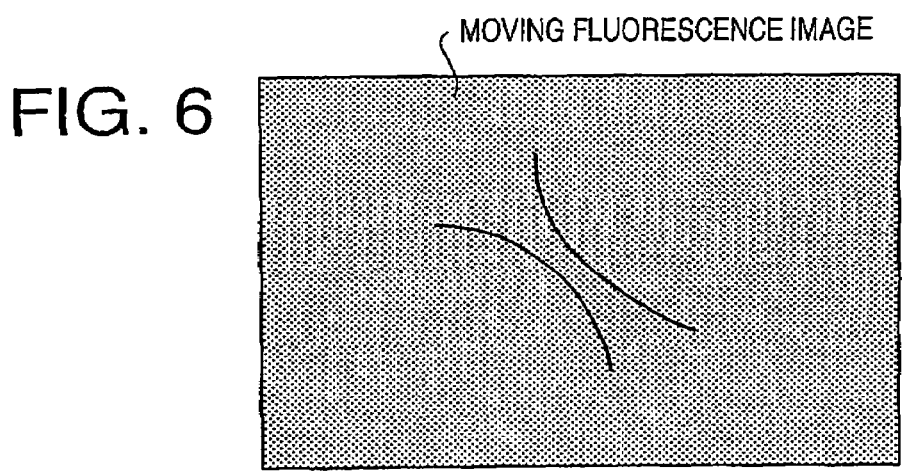
FIG. 6 shows an example of a screen displayed on the monitor in a fluorescence image display mode.

The pre-signal-processing circuit 57 allows the first and second memories 58a, 58b to store the fluorescence signals, based on the signals from the timing controller 71. The post-signal-processing circuit 59, based on the signals from the timing controller 71, reads out the image signals from the first and second memories 58a, 58b to convert the image signals to the video signals, displaying a single fluorescence image as a moving image on the monitor 60. FIG. 6 shows an example of the screen that is displayed on the monitor 60 in the fluorescence image display mode.

Figure 7:
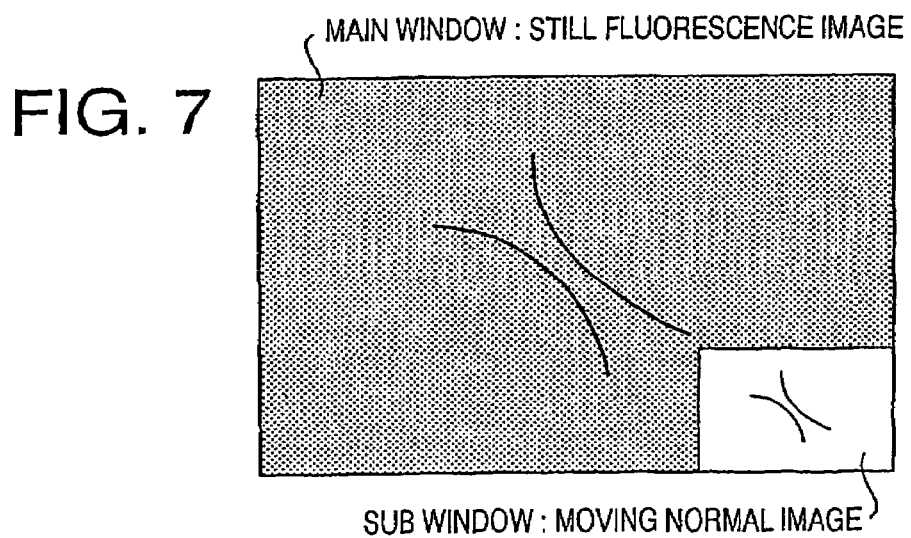
FIG. 7 shows an example of a screen displayed on the monitor when a still image switch is turned ON in a fluorescence image display mode.

If the still image switch 72 is turned ON in the fluorescence image display mode, the system controller 70 keeps the location of the unit 40 on the white light path, and the timing controller 71 controls the second motor driver 54 to rotate the rotary shutter 37, and controls the lamp driving power supply 51 to let the white light source 30 emit the white light, and further controls the laser driver to turn OFF the excitation light. Furthermore, the timing controller 71 forbids to write the image signals to the first and second image memories 58a, 58b, and allows the imaging device 13 to keep taking images and the third and fourth memories 58c, 58d to store the normal image signals obtained by white light irradiation. Based on the signals from the timing controller 71, the post-signal-processing circuit 59 reads out the same signals repeatedly from the first and second memories to display the still fluorescence image in the main window on the monitor 60, and further reads out the signals rewritten sequentially from the third and fourth memories 58c, 58d to generate the video signals, which are used to display the moving normal image in the sub window on the monitor 60. FIG. 7 shows an example of the screen that is displayed on the monitor 60 when the still image switch 72 is turned ON in the fluorescence image display mode.

When the fluorescence mode switch 73 is turned ON and the system is set up in the simultaneous display mode by the switches on the switch panel 23, the system controller 70 controls the third motor driver 55 to drive the unit driving motor 42 so that the unit 40 is shifted to the point on the white light path, and further controls the lamp driving power supply 51 to let the white light source emit continuously. The timing controller 71 controls the second motor driver 54 to rotate the shutter driving motor 38, and further controls the laser driver 52 to turn OFF the excitation light source 33 while the window 37a of the rotary shutter 37 is located on the white light path (while the white light is introduced into the light guide) and generate the excitation light while the shielding part of the rotary shutter 37 is located on the white light path (while the white light is not introduced into the light guide). Thereby, an object is alternately irradiated with the white light and the excitation light. The imaging device 13 provided at the tip of the fluorescence observation endoscope alternately takes the normal image of the body cavity wall illuminated with the white light and the fluorescence image of the body cavity wall excited by the excitation light. The image signals outputted from the imaging device 13 is inputted into the pre-signal-processing circuit 57 through the cable driver 15 and the signal cable 18.

Figure 8:
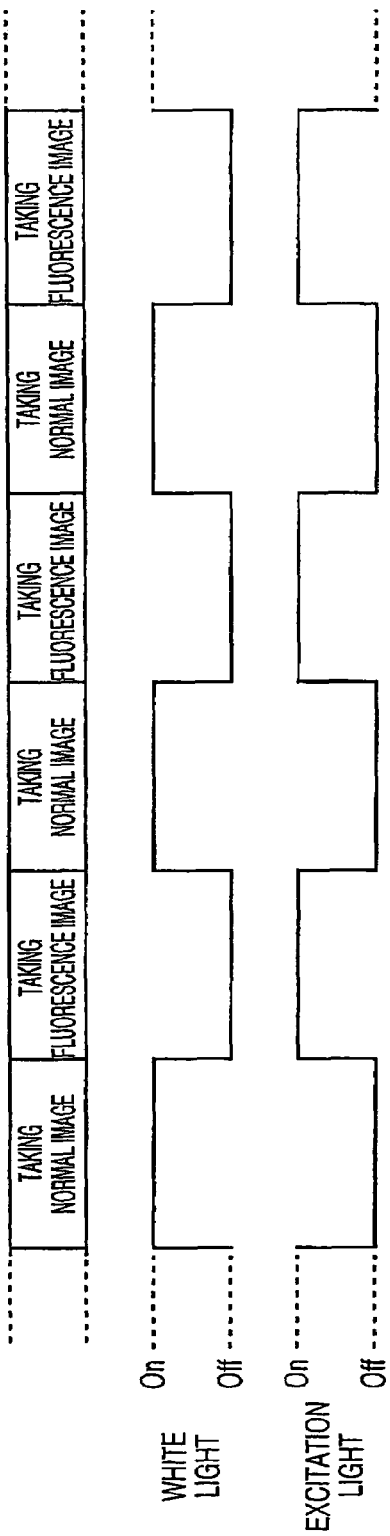
FIG. 8 is a chart illustrating the respective irradiation timings of white light and excitation light and the respective timings when the two kinds of image data are outputted from an imaging device in a simultaneous display mode.

FIG. 8 is a chart pattern showing the respective irradiation timings of the white light and the excitation light in the simultaneous display mode and the timing when image data is outputted from the imaging device. As shown in FIG. 8, the normal color image is taken while the white light is applied and the excitation light is not applied, and the fluorescence image is taken while the white light is not applied and the excitation light is applied.

Figure 9:
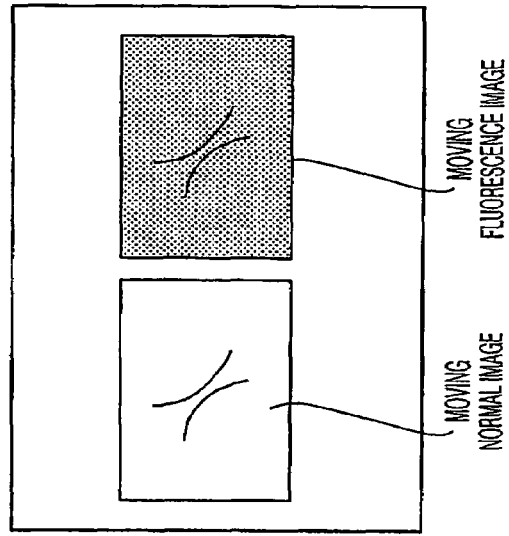
FIG. 9 shows an example of a screen displayed on the monitor in the simultaneous display mode.
Figure 10:
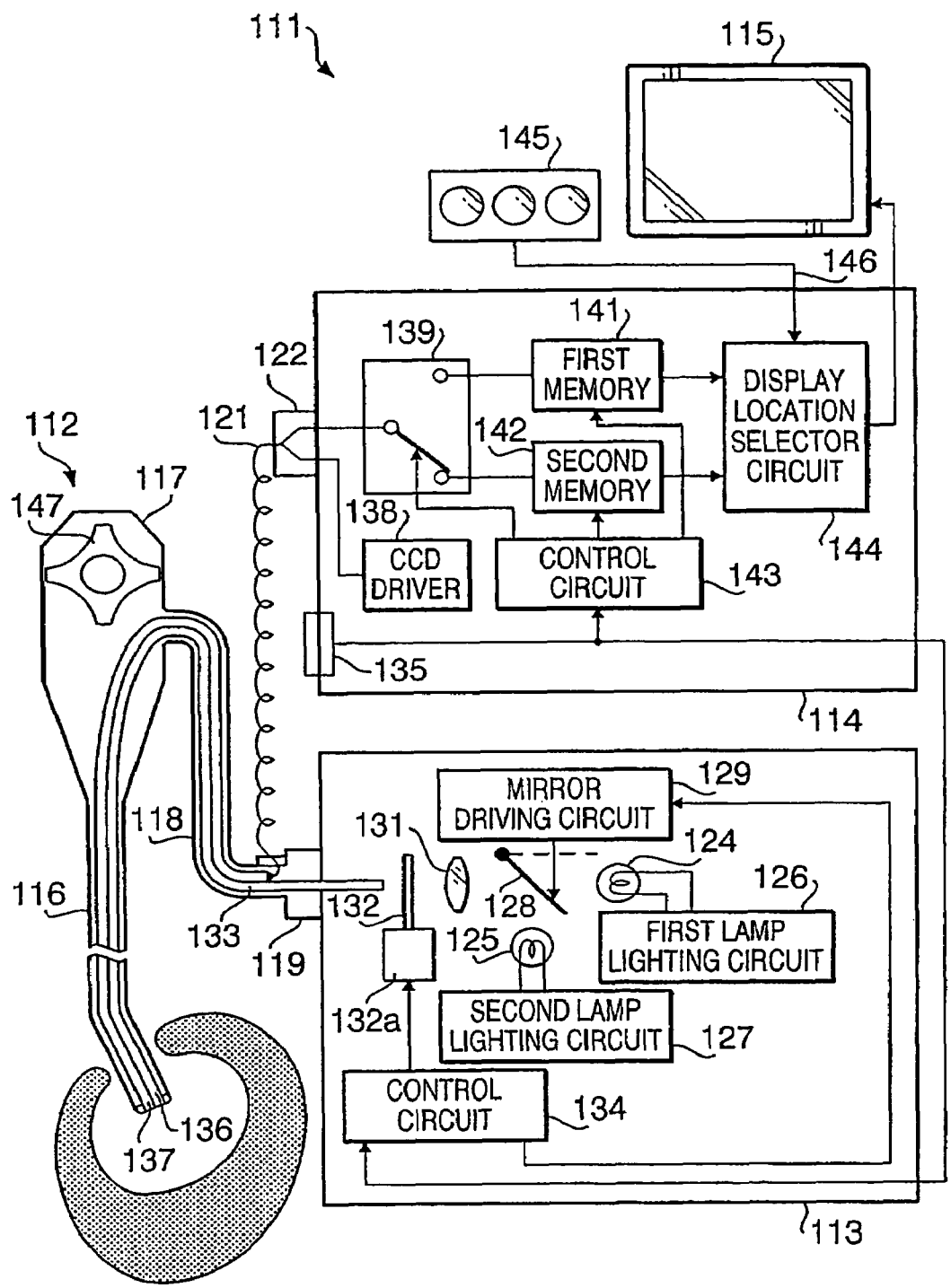
FIG. 10 is a block diagram showing a configuration of a conventional electronic endoscope system.

Based on the signals from the timing controller 71, the pre-signal-processing circuit 57 allows the first image memory 58a to store the normal image signals and the second memories to store the fluorescence image signals. Based on the signals from the timing controller 71, the post-signal-processing circuit 59 reads out the respective image signals from the first and second memories, and performs scan conversion for the respective image signals, which are then displayed as a moving normal image and a moving fluorescence image, respectively, side by side in the same-sized windows on the monitor 60. FIG. 9 shows an example of the screen that is displayed on the monitor 60 in the simultaneous display mode.

If the still image switch is turned ON in the simultaneous display mode, the system controller 70 keeps the location of the unit 40 on the white light path, and the timing controller 71 controls the second motor driver 54 to rotate the rotary shutter 37, and controls the lamp driving power supply 51 to let the white light source emit, and further controls the laser driver 52 to turn OFF the excitation light source. The timing controller 71 allows the first and second image memories 58a, 58b to be write-protected, and further allows the imaging device 13 to keep taking images and the third image memory 58c to store the normal image signals obtained by the white light irradiation. Based on the signals from the timing controller 71, the post-signal-processing circuit 59 reads out the same signals from the second image memory 58b repeatedly to display the still fluorescence image in the main window, and further reads out the signals rewritten sequentially from the third image memory 58c to generate the video signals, which are displayed as a moving normal image in the sub window on the monitor 60. That is to say, the display on the monitor 60 in this case is the same as shown in FIG. 7.

When the still image switch is turned ON in the fluorescence image display mode, supposing that the still fluorescence image and the moving fluorescence image are displayed in the main and sub windows, respectively, since the fluorescence image generally has low brightness, the function of the sub window that is displayed for purposes such as ensuring the endoscope tip location and averting a risk may not be carried out adequately. In this embodiment, when the still fluorescence image is displayed, the colored normal image is displayed in the sub window. Therefore, the sub window is displayed so clearly as to carry out the function thereof adequately.

In addition, it is due to the following reasons to shift the unit 40 to the point out of the white light path while taking the color normal image with the white light. If the unit 40 is located on the white light path, it is necessary to stop the rotary shutter 52 at a point that the window 52a is just on the white light path, or to keep the rotary shutter rotating, in order to transmit the white light. However, since it is difficult to determine the stop location of the shutter driving motor 53 precisely under open loop control, a position detector is needed specially in order to determine the stop location. On the other hand, since if the rotary shutter is rotated, the white light irradiation time will be half as much as the total time that the white light is emitted, the time to take images by the imaging device is reduced by half. Accordingly, the image resolution in terms of the number of frames of the moving image is halved. For these reasons, the dichroic mirror 36 and the rotary shutter 37, which are integrated with the unit 40, are shifted as one to the point out of the white light path during the normal observation. Therefore, it is not necessary to prepare for the position detector specially, and furthermore, it is possible to obtain twice as much resolution as the case where the rotary shutter is rotated.

The present disclosure relates to the subject matter contained in Japanese Patent Application No. P2004-191931, filed on Jun. 29, 2004, which is expressly incorporated herein by reference in its entirely.

What is claimed is:

1. An electronic endoscope system used for observing living tissues inside a body cavity, comprising:

a single imaging device that receives an optical image and outputs an image signal corresponding to the received optical image;

an illuminating device having a white light source emitting white light and an excitation light source that emits excitation light having a predetermined wavelength, the living tissues emitting autofluorescence when irradiated with the excitation light, the illuminating device further including a rotary shutter, wherein the rotary shutter and a beam combiner are provided on a movable unit configured to move in a direction perpendicular to a path of the white light such that the rotary shutter does not interfere with the white light, the beam combiner combining both light paths of the white light and the excitation light;

an image forming system that forms said optical image of the living tissues illuminated with each of the white light and the excitation light on the imaging device;

an illuminating control system that controls the illuminating device such that the white light source and the excitation light source illuminate the living tissues alternately at every predetermined period;

an image processing system that receives the image signal outputted by the single imaging device, the image processing system configured to obtain a normal image when the living tissues are illuminated with the white light and a fluorescence image when the living tissues are irradiated with the excitation light;

a display device configured to display the normal image and the fluorescence image; and a display control system that controls the display device such that the normal image is displayed in a first displaying area of the display device and the fluorescence image is displayed in a second displaying area, the predetermined period being determined so that the normal image and the fluorescence image appear to be displayed simultaneously as moving images.

2. The electronic endoscope system according to claim 1, wherein the rotary shutter is provided in front of the white light source, the rotary shutter having a light transmitting area and a light blocking area, the white light intermittently illuminating the living tissues as the rotary shutter rotates.

3. The electronic endoscope system according to claim 2, wherein the illuminating device includes an excitation light source driver that intermittently turns ON/OFF the excitation light source synchronously with the blocking/transmitting operation of the rotary shutter.

4. The electronic endoscope system according to claim 1, wherein the image processing system includes:

a pre-signal-processing element that processes the image signals received from the imaging device;

at least two image memories that temporarily store the image signals outputted from the pre-signal-processing element; and a post-signal-processing element that transforms the image signals outputted from the image memories into standardized video signals which are allowed to be displayed on the display device.

5. The electronic endoscope system according to claim 1, wherein the image forming system includes:

an objective lens that receives light from the living tissues and forms an image thereof; and an excitation light cut filter that is provided between the objective lens and the imaging device, wherein the excitation light cut filter eliminates the wavelength components equivalent to the excitation light from light directed to the imaging device from the objective lens.

6. The electronic endoscope system according to claim 5, wherein the excitation light source emits near-ultraviolet light.

7. An electronic endoscope system used for observing living tissues inside a body cavity, comprising:

a single imaging device that receives an optical image and outputs an image signal corresponding to the received optical image;

an illuminating device having a white light source emitting white light and an excitation light source that emits excitation light having a predetermined wavelength, the living tissues emitting autofluorescence when irradiated with the excitation light, the illuminating device further including a rotary shutter, wherein the rotary shutter and a beam combiner are provided on a movable unit configured to move in a direction perpendicular to a path of the white light such that the rotary shutter does not interfere with the white light, the beam combiner combining both light paths of the white light and the excitation light;

an image forming system that forms said optical image of the living tissues illuminated with each of the white light and the excitation light on the imaging device;

an image processing system that receives the image signal outputted by the single imaging device, the image processing system configured to obtain a normal image when the living tissues are illuminated with the white light and a fluorescence image when the living tissues are irradiated with the excitation light;

a display device configured to display the normal image and the fluorescence image on a first display area and a second display area on the display device, respectively; and an operable member to be operated by a user when a still image is to be displayed on the display device, wherein, when a moving fluorescence image is to be displayed on the display device, the white light source is powered OFF and the excitation light source is powered ON, wherein, if the operable member is operated when the moving fluorescence image is displayed on the display device, the excitation light source is powered OFF and the white light source is turned ON, the fluorescence image which was obtained immediately before the excitation light source is powered OFF and is repeatedly displayed on the second display area of the display device as a still fluorescence image, the imaging device outputs the image signal corresponding to the optical image of the living tissues illuminated with the white light, the image processing system obtains the normal image of the living tissues which is displayed on the first display area of the display device, and the normal image and the fluorescence image are displayed on the display device simultaneously.

8. The electronic endoscope system according to claim 7, wherein the first display area is smaller than the second display area.

9. The electronic endoscope system according to claim 8, wherein the second display area includes the first display area.

10. The electronic endoscope system according to claim 7, wherein the rotary shutter is provided in front of the white light source, the rotary shutter having a light transmitting area and a light blocking area, the white light intermittently illuminating the living tissues as the rotary shutter rotates.

11. The electronic endoscope system according to claim 10, wherein the illuminating device includes an excitation light source driver that intermittently turns ON/OFF the excitation light source synchronously with the blocking/transmitting operation of the rotary shutter.

12. The electronic endo scope system according to claim 7, wherein the image processing system includes:

a pre-signal-processing element that processes the image signals received from the imaging device;

at least two image memories that temporarily store the image signals outputted from the pre-signal-processing element; and a post-signal-processing element that transforms the image signals outputted from the image memories into standardized video signals which are allowed to be displayed on the display device.

13. The electronic endo scope system according to claim 7, wherein the image forming system includes:
an objective lens that receives light from the living tissues and forms an image thereof; and
an excitation light cut filter that is provided between the objective lens and the imaging device,
wherein the excitation light cut filter eliminates the wavelength components equivalent to the excitation light from light directed to the imaging device from the objective lens.

14. The electronic endoscope system according to claim 13, wherein the excitation light source emits near-ultraviolet light.

15. An electronic endoscope system used for observing living tissues inside a body cavity, comprising:
an electronic endoscope including an insertion part configured to be inserted in the body cavity, a light guide which transmits light to a tip of the insertion part through the insertion part, and a single imaging device which receives light from the living tissues illuminated with light transmitted by the light guide;
an illuminating device having a white light source emitting white light and an excitation light source that emits excitation light having a predetermined wavelength, the living tissues emitting autofluorescence when irradiated with the excitation light,
the illuminating device further including a rotary shutter, wherein the rotary shutter and a beam combiner are provided on a movable unit configured to move in a direction perpendicular to a path of the white light such that the rotary shutter does not interfere with the white light, the beam combiner combining both light paths of the white light and the excitation light;
an image forming system that forms an optical image of the living tissues illuminated with the white light and the excitation light on the imaging device;
an image processing system that obtains a normal image when the living tissues are illuminated with the white light and a fluorescence image when the living tissues are irradiated with the excitation light;
a display device configured to display the normal image and the fluorescence image; and
a controller that controls the illuminating device to alternately introduce the white light and the excitation light into the light guide when the electronic endoscope operates in a first mode, wherein
the image processing system generates both normal image signals and fluorescence image signals when the electronic endoscope operates in the first mode, wherein
the controller controls the illuminating device to introduce only the white light into the light guide when the electronic endoscope operates in a second mode, and wherein
the display device displays a still fluorescence image based on the fluorescence image signal generated immediately before the first mode switches to the second mode, and further displays a moving normal image based on the normal image signal when the body cavity wall is illuminated with the white light.

* * * * *